US012778387B2

(12) United States Patent
Wieters et al.

(10) Patent No.: US 12,778,387 B2
(45) Date of Patent: Nov. 3, 2026

(54) ENDOSCOPE AND METHOD OF MANUFACTURING A SEALED UNIT OF AN ENDOSCOPE

(71) Applicant: OLYMPUS Winter & Ibe GmbH, Hamburg (DE)

(72) Inventors: Martin Wieters, Barsbttelue (DE); Nils Torkuhl, Hamburg (DE); Mathias Laser, Hamburg (DE)

(73) Assignee: OLYMPUS Winter & Ibe GmbH, Hamburg (DE)

( * ) Notice: Subject to any disclaimer, the term of this patent is extended or adjusted under 35 U.S.C. 154(b) by 650 days.

(21) Appl. No.: 18/127,045

(22) Filed: Mar. 28, 2023

(65) Prior Publication Data

US 2023/0309797 A1 Oct. 5, 2023

Related U.S. Application Data

(60) Provisional application No. 63/325,252, filed on Mar. 30, 2022.

(51) Int. Cl.

| | |
|---|---|
| ***A61B 1/00*** | (2006.01) |
| ***A61B 1/05*** | (2006.01) |
| *A61M 25/00* | (2006.01) |

(52) U.S. Cl.

CPC .............. *A61B 1/0011* (2013.01); *A61B 1/05* (2013.01); *A61M 2025/0006* (2013.01)

(58) Field of Classification Search

CPC ................... A61B 1/0011; A61B 1/05; A61M 2025/0006; G02B 23/2476

See application file for complete search history.

(56) References Cited

U.S. PATENT DOCUMENTS

| | | | | |
|---|---|---|---|---|
| 2018/0020904 A1 | 1/2018 | Wieters et al. | | |
| 2020/0196835 A1* | 6/2020 | Qvist | ................... | A61B 1/0011 |
| 2020/0288953 A1 | 9/2020 | Sørensen et al. | | |
| 2021/0127958 A1* | 5/2021 | Wakabayashi | ....... | A61B 1/0011 |

FOREIGN PATENT DOCUMENTS

| | | |
|---|---|---|
| CN | 111 134 596 A | 5/2020 |
| JP | S59-121304 A | 7/1984 |
| JP | 2020008649 A * | 1/2020 |

OTHER PUBLICATIONS

German Office Action dated Dec. 14, 2022 received in 10 2022 107 674.1.

European Search Report dated Jul. 27, 2023 received in 23 16 3006.

* cited by examiner

*Primary Examiner* — Michael J Carey

*Assistant Examiner* — Christen A. Sharpless

(74) *Attorney, Agent, or Firm* — Scully, Scott, Murphy & Presser, P.C.

(57) ABSTRACT

An endoscope including: a handle, an elongated shaft, and a video camera disposed in the shaft. The elongated shaft having a unit including a plurality of nested tubes. The plurality of nested tubes including a first tube and a second tube at least partially disposed within the first tube, the first tube and the second tube being fixed to one another through adhesive bonding. The first tube having a first bore formed in the first tube, the first bore communicating with a first gap between the first tube and the second tube, and an adhesive is provided in the first gap.

20 Claims, 3 Drawing Sheets

ENDOSCOPE AND METHOD OF MANUFACTURING A SEALED UNIT OF AN ENDOSCOPE

CROSS-REFERENCE TO RELATED APPLICATION

The present application is based upon and claims the benefit of priority from U.S. Provisional Application No. 63/325,252 filed on Mar. 30, 2022, the entire contents of which is incorporated herein by reference.

BACKGROUND

Field

The present disclosure relates to an endoscope and a method of manufacturing a sealed unit of an endoscope.

Prior Art

Endoscopes are used in surgery since many years, for providing visual or surgical access to internal cavities of a patient. Endoscopes usually comprise a handle and an elongated shaft. Depending on the intended application, the shaft can be flexible or rigid.

In modern video endoscopes, a video camera is disposed in the shaft, usually at the distalmost end thereof. The video camera usually comprises an objective lens, an imaging chip for converting an image generated by the objective lens into electronic signals, and processing circuitry for processing the electronic signals.

Due to the complex and expensive design, video endoscopes are usually provided for multiple use, and therefore need to undergo careful reprocessing, so that cross-contamination of patients by pathogens can be prevented. Such reprocessing can include subjecting the endoscope to hostile conditions including high pressure, high moisture, and aggressive chemicals. For protecting delicate optical and electronic components of the endoscope against such hostile conditions, they are provided in a separate sealed unit including a plurality of nested tubular members. Such tubular members are often fixed to one another through adhesive bonding. Such sealed unit is sometimes referred to as R-unit.

Manufacture of the sealed unit comes with certain challenges. For bonding the nested tubular members with each other, a layer of an adhesive agent is usually applied to the outer surface of an inner tubular member, and then the inner tubular member is slid into an outer tubular member. In this process, a part of the adhesive agent layer is peeled off the inner tubular member and forms drops or a continuous a rope at a front surface of the outer tubular member. Such excess adhesive agent needs to be removed before the manufacturing process can be continued. Further, the adhesive agent between the inner and outer tubular members cannot be irradiated with UV radiation for rapid setting, so a thermosetting adhesive must be used. However, when applying heat to the tubular members before they are firmly fixed, positioning of the tubular members may be affected by thermal expansion.

Endoscopes may include other units comprising nested tubular members, which need not necessarily be sealed units. For such units, similar manufacturing challenges may apply.

SUMMARY

Therefore, an object is to provide an improved endoscope, and an improved method of manufacturing a unit, such as a sealed unit, of an endoscope.

Provided is an endoscope comprising a handle, an elongated shaft, and a video camera disposed in the shaft, the endoscope comprising a unit including a plurality of nested tubular members, the nested tubular members comprising an outer tubular member and an inner tubular member being fixed to one another through adhesive bonding, wherein a bore is formed in the outer tubular member, and an adhesive agent is provided in a gap between the outer tubular member and the inner tubular member. The bore in the outer tubular member facilitates injection of the adhesive agent into the gap. The adhesive agent may be provided in the gap in an area surrounding the bore. The adhesive agent may be spread in the gap by capillary action. The unit may be a sealed unit of the video camera of the endoscope.

The inner tubular member may comprise a recess in an area corresponding to the bore of the outer tubular member. The recess may create a cavity between the inner tubular member and the outer tubular member, which can receive adhesive agent injected through the bore. From the cavity, the adhesive agent can easily be spread further into the gap by capillary action. After setting of the adhesive agent, the adhesive agent in the cavity can create a positive lock between the inner tubular member and the outer tubular member. The recess may be a flat portion, a cut, a counterbore, or the like.

A plurality of bores may be formed along a circumference of the outer tubular member, for facilitating better spreading of the adhesive agent. The adhesive agent may form a gapless adhesive layer fully extending around the circumference of the inner tubular member. The gapless adhesive layer may provide secure fixing and sealing between the inner tubular member and the outer tubular member.

The plurality of nested tubular members may further comprise a middle tubular member nested between the outer tubular member and the inner tubular member. One or more bores may be formed in the middle tubular member, so that the bores of the outer tubular member and the bores of the middle tubular member overlap. Here, the term “overlap” is to be understood as indicating that a bore of the outer tubular member and a corresponding bore of the middle tubular member form a continuous passage reaching from an outer surface of the outer tubular member to an outer surface of the inner tubular member. Such overlap of the bores of the middle tubular member may be circumferentially and/or longitudinally offset against the bores of the outer tubular member.

The bores of the middle tubular member may be smaller in diameter than the bores of the outer tubular member. The bores of the middle tubular member may be offset against the bores of the outer tubular member, so that the bores of the middle tubular member and the bores of the outer tubular member partially overlap. With the bores of the middle tubular member and the bores of the outer tubular member partially overlapping, a cavity is formed between the inner and the outer tubular member, from which the adhesive agent can easily be spread into an inner gap between the inner tubular member and the middle tubular member, and into an outer gap between the middle tubular member and the outer tubular member.

The bores of the middle tubular member may be larger in diameter than the bores of the outer tubular member. With the bores of the middle tubular member being larger than the bores of the outer tubular member, a cavity is formed between the inner and the outer tubular member, from which the adhesive agent can easily be spread into an inner gap between the inner tubular member and the middle tubular member, and into an outer gap between the middle tubular member and the outer tubular member.

The adhesive agent may comprise a first type adhesive agent applied in the area of at least a first one of the plurality of bores, and a second type adhesive agent applied in the area of at least a second one of the plurality of bores. The first type adhesive agent may be a UV-setting adhesive agent. The second type adhesive agent may be a thermosetting adhesive agent. The second type adhesive agent may have a higher glass transition temperature than the first type adhesive agent. The UV-setting adhesive agent in the at least one first bore may first be set through irradiating with UV radiation, fixing the tubular members to each other. Then, the thermosetting adhesive agent may be set through heating the tubular members, while the previously set UV-setting adhesive agent prevents de-positioning of the tubular members due to thermal expansion, shrinking of adhesive, or similar effects.

Further provided is a method of manufacturing a unit of nested tubular members of an endoscope, comprising providing an inner tubular member and an outer tubular member; forming one or more bores in the outer tubular member; positioning the inner tubular member in the outer tubular member, so that a gap is formed between the inner and outer tubular members; applying an adhesive agent into the bores of the outer tubular member; spreading the adhesive agent in the gap by capillary action; and setting the adhesive agent. By applying the adhesive agent after positioning the tubular members, peeling of excess adhesive agent can be avoided, so that no additional cleaning step is required during manufacture of the unit.

The method may further comprise forming one or more recesses on the inner tubular member, and positioning the inner tubular member in the outer tubular member so that the recesses of the inner tubular member correspond to the bores in the outer tubular member. The recesses may form cavities between the inner tubular member and the outer tubular member. The recesses may comprise flat portions, cuts, counterbores, or the like. Flat portions may easily be formed on the outer surface of the inner tubular member by milling.

The method may further comprise providing a middle tubular member; forming one or more bores in the middle tubular member; and positioning the middle tubular member and the inner tubular member in the outer tubular member, so that the bores of the middle tubular member and the bores of the outer tubular member overlap.

The middle tubular member may be positioned in the outer tubular member so that the bores of the middle tubular member are offset against the bores of the outer tubular member, and only partially overlap with the bores of the outer tubular member.

The method may include forming a plurality of bores in the outer tubular member and optionally in the middle tubular member, wherein the applying, spreading, and setting of the adhesive agent comprise applying a first type adhesive agent to at least a first one of the bores; setting the first type adhesive agent; applying a second type adhesive agent to at least a second one of the bores; spreading the second type adhesive agent in the gap through capillary action; and setting the second type adhesive agent.

The first type adhesive agent may be a UV-setting adhesive agent, and setting the first type adhesive agent may include irradiating the first type adhesive agent with UV radiation. The second type adhesive agent may be a thermosetting adhesive agent, and setting the second type adhesive agent may include heating the second type adhesive agent.

Some examples of the present disclosure are described in the following illustrative drawings. The examples described are provided for better understanding, and are not supposed to be exhaustive, or to limit the scope of the appended claims in any way.

DETAILED DESCRIPTION

Figure 1:
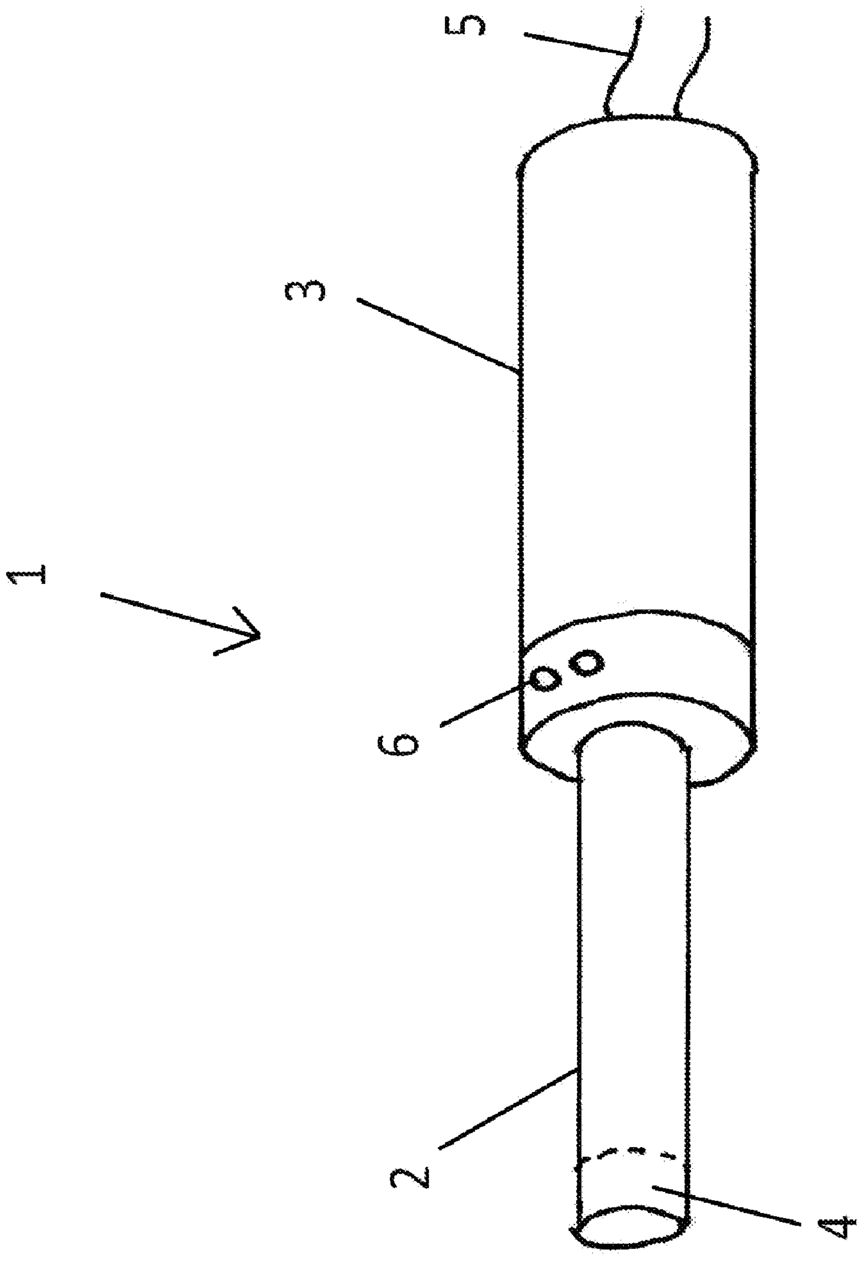
FIG. 1 illustrates a perspective view of an endoscope.

FIG. 1 shows an endoscope 1 comprising an elongate shaft 2 and a handle 3. In the distal area of the shaft 2, a video camera 4 is provided. Video signals from the video camera 4 are communicated to external video processing circuitry (not shown) through a cable 5 for processing, display, and/or recording. Cable 5 may also supply current and illumination light to the endoscope from an external source (not shown).

Figure 2:
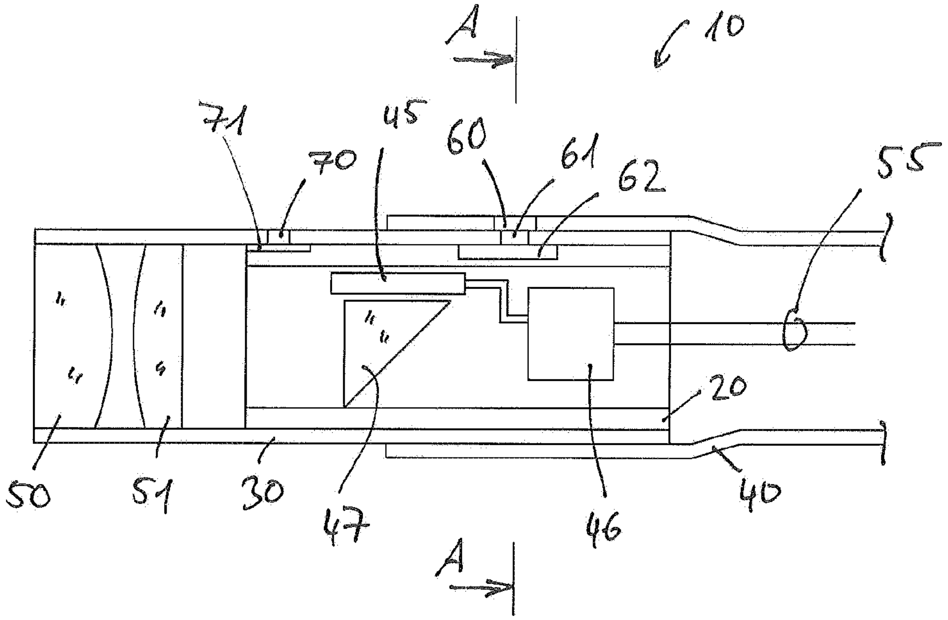
FIG. 2 illustrates a longitudinal sectional view of a sealed unit of the endoscope in FIG. 1.
Figure 3:
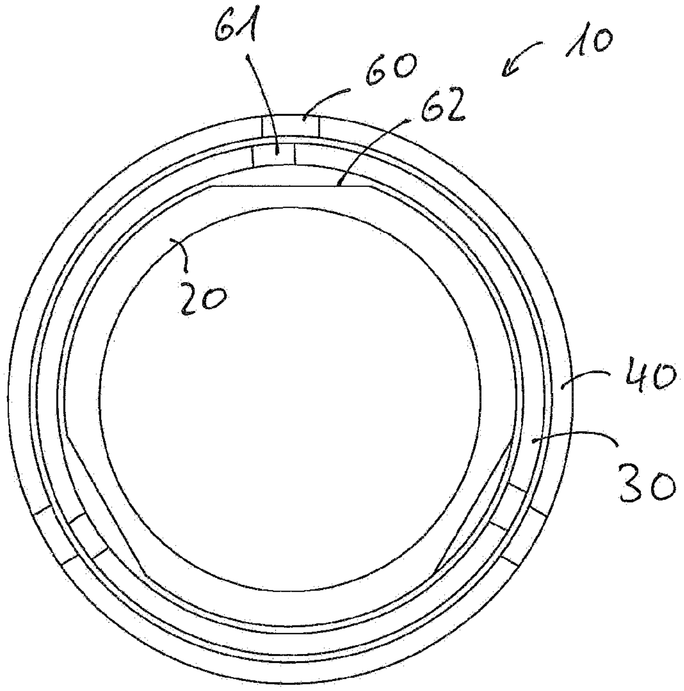
FIG. 3 illustrates a sectional view of the sealed unit of FIG. 2 as viewed along section A-A in FIG. 2.

For protecting optical and electronic components of the video camera 4 against hostile environmental influences, the endoscope 1 comprises a sealed unit 10, which is shown in FIGS. 2 and 3. FIG. 2 shows the sealed unit 10 in a longitudinal section. FIG. 3 shows the sealed unit 10 in a cross section along the plane A-A shown in FIG. 2.

The sealed unit 10 comprises a plurality of nested tubular members 20, 30, 40 ("tubes"). An inner tubular member 20 ("inner tube") houses an imaging chip 45 ("image sensor"), pre-processing circuitry 46, and a prism 47. The inner tubular member is sometimes referred to as a C-holder. A middle tubular member 30 ("middle tube") houses the inner tubular member 20 and lenses 50, 51 of an objective lens system. The middle tubular member 30 is sometimes referred to as an objective system tube. The outer tubular member 40 ("outer tube") houses the middle tubular member and extends in the shaft 2 in a proximal direction. Connection lines 55 extend through the outer tubular member 40 to a plug (not shown), which hermetically seals the outer tubular member 40 at the proximal end The outer tubular member 40 is sometimes referred to as a boss tube.

In the present embodiment, the tubular units 20, 30, 40 are shown to have circular cross sections. Other cross sections may also be possible, like elliptic, oval, or the like. The tubular members 20, 30, 40 may also have prismatic cross sections. While not shown in FIG. 3, the inner tubular member 20 may have an inner structure configured to precisely hold the prism 47 and the imaging chip 45.

For manufacturing the sealed unit 10, the inner tubular member 20 with the imaging chip 45, the prism 47, and the pre-processing circuitry is first placed in the middle tubular member 30 with the lenses 50, 51, and carefully positioned so that an image is sharply focused on the imaging chip 45. Then, the inner tubular member 20 and the middle tubular member 30 are placed in the outer tubular member 40.

The tubular members 20, 30, 40 are fixed to one another by adhesive bonding. Therefore, an adhesive agent (adhesive) is injected into annular gaps between respective tubular members as shown in FIG. 3. The size of the gaps in FIG. 3 is not shown in scale, but is exaggerated for better visibility.

Bores 60 in the outer tubular member 40 and bores 61 in the middle tubular member 30, overlapping each other, are provided for applying the adhesive agent. Such overlap of the bores 61 of the middle tubular member 30 may be circumferentially and/or longitudinally offset against the bores 60 of the outer tubular member 40.

Further, recesses 62 are provided on the outer surface of the inner tubular member 20. The recesses 62 may have the shape of a fat portion.

Bores 60, 61 and recess 62 form a passage and a cavity, into which the adhesive agent is injected. After injection, the adhesive agent will spread in the respective gaps between the tubular members 20, 30, 40 by capillary action, i.e., the adhesive agent will be drawn into the gaps surrounding the bores 60, 61. By providing an appropriate number and size of bores 60, 61 and recesses 62 around the circumference of the sealed unit, the adhesive agent forms a continuous layer in the gap, thereby securely fixing and sealing the tubular members 20, 30, 40 to and against each other.

When adhesive agent is injected to completely fill the cavity formed by bores 60, 61 and recesses 62, the adhesive agent will first spread to both an inner gap between the inner tubular member 20 and the middle tubular member 30, and an outer gap between the middle tubular member 30 and the outer tubular member 40. After some adhesive agent has been drawn from the cavity, the bore 60 is no longer filled with adhesive agent. For enabling further adhesive agent still being drawn into the outer gap, the bores 60, 61 are offset, or staggered, against each other, so that they only partly overlap. This forms an adhesive agent reservoir between an inner surface of the outer tubular member 40 and an outer surface of the inner tubular member 20, from which further adhesive agent can be drawn into the outer gap. In the embodiment shown, the bores 60 of the outer tubular member are larger in diameter than the bores 61 of the middle tubular member. A similar effect can be achieved by providing the bores 61 of the middle tubular member 30 with a larger diameter than the bores 60 of the outer tubular member 40 (not shown). The flat portions 62 serve to further increase the volume of the adhesive agent receiving cavity, so that more adhesive agent may be injected. The recesses 62 further provide a positive lock between the middle tubular member 30 and the inner tubular member 20. While not shown, similar recesses may be provided on the outer surface of middle tubular member 30.

After the adhesive agent is spread in the gaps, it is cured for fixing the tubular members 20, 30, 40. As the adhesive agent cannot be irradiated with UV light in the gaps, a thermosetting adhesive agent is preferably used. As one example, an epoxy resin can be used as adhesive agent. After being set, epoxy resins can tolerate the elevated temperatures to be expected during reprocessing of the endoscope 1, e.g., in an autoclave.

For setting the thermosetting resin, the sealed unit needs to be subjected to high temperatures before the adhesive agent is fully cured, which may result in displacement of the respective tubular members 20, 30, 40 and may affect the optical quality of the endoscope 1. For preventing such displacement, the adhesive bonding of the tubular members 20, 30, 40 may be done in several steps, using different types of adhesive agents.

In a first step, an UV curing adhesive, for example an acrylic resin, may be applied to a first set of bores 60, 61 and respective flat portion. The UV curing adhesive may be applied with a relatively high viscosity or thixotropy, so that it does not significantly spread into the gaps surrounding the first set of bores 60, 61. The UV curing adhesive may then be cured by irradiating with IV radiation, forming a first adhesive bond between the tubular members 20, 30, 40.

In a second step, a low viscosity thermosetting adhesive agent is applied to the remaining sets of bores 60, 61 and flat portions, so that it spreads into the gaps through capillary action. After the thermosetting adhesive agent is fully spread, the nested tubular members are heated in an oven for fully setting the thermosetting adhesive agent, thereby completing the adhesive bond, while the previously cured UV setting adhesive prevents displacement of the respective tubular members.

The UV curing adhesive may be applied to a bore or bores axially offset from the bores 60, 61, to which the thermosetting adhesive agent is applied. As shown in FIG. 2, an additional bore 70 may be provided in the middle tubular member 30 distally from a distal end of the outer tubular member 40, and an additional flat portion 71 may be provided on the outer surface of the inner tubular member 20. The UV curing adhesive may be applied to the cavity formed by the bore 70 and the flat portion 71, and then be cured for fixing the inner tubular member 20 and the middle tubular member 30 with each other. Then, the thermosetting adhesive agent may be applied to the bores 60, 61 and the recesses 62. When the thermosetting adhesive agent is subsequently cured by heating, the previously cured adhesive bond between the inner tubular member 20 and the middle tubular member 30 prevents displacement of these tubular members, while a possible displacement of the middle tubular member 20 in the outer tubular member 40 is much less critical for the optical quality of the endoscope 1.

The sequence of the above steps may be varied. For example, the U V curing adhesive may be applied and cured after placement and adjustment of the inner and middle tubular members 20, 30, the imaging chip 45, the prism 47, and the lenses 50, 51, but before the so-formed sub-unit is placed inside the outer tubular member 40.

Figure 4:
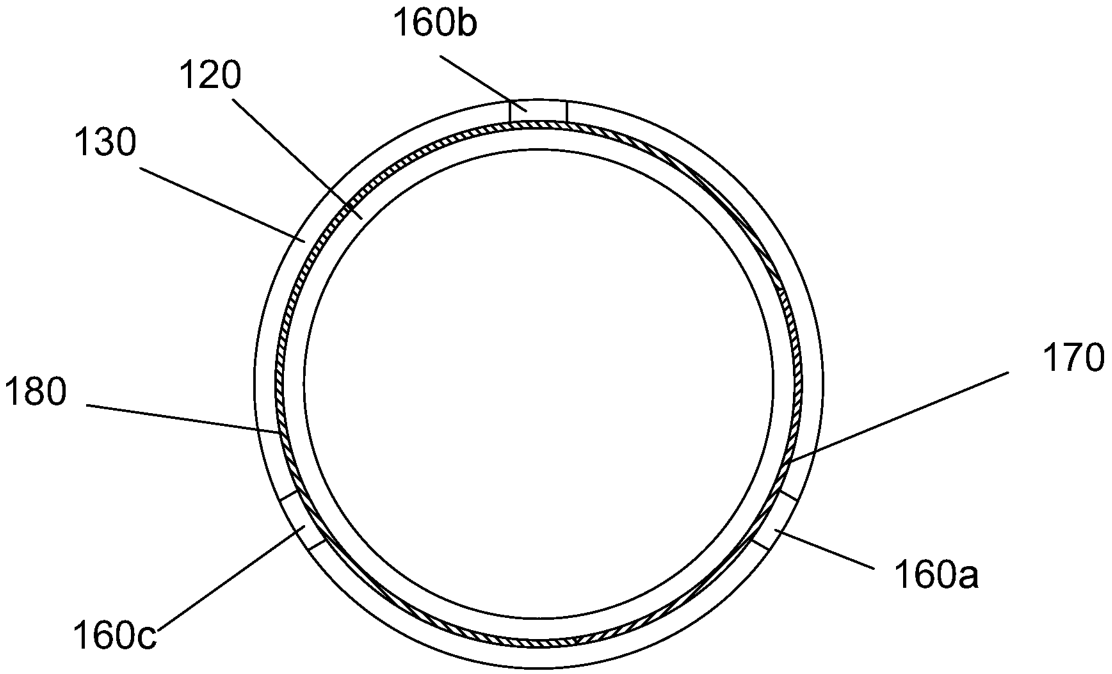
FIG. 4 illustrates an alternative section view of the sealed unit of FIG. 2.

FIG. 4 shows a sectional view of a further sealed unit. The sealed unit illustrated in FIG. 4 comprises an inner tubular member 120 and an outer tubular member 130, and a gap between the inner tubular member 120 and the outer tubular member 130. The outer tubular member 130 comprises three bores 160*a*, 160*b*, 160*e* along the circumference thereof, which can be equally spaced about such circumference. A first adhesive 170 fills the gap in an area surrounding a first one of the bores 160*a*, and a second adhesive 180 fills the gap in an area surrounding a second and a third one of the bores 160*b*, 160*c*. The first adhesive 170 may be an UV-setting adhesive. The second adhesive 180 may be a thermosetting adhesive.

While the disclosed embodiments show a sealed unit having three nested tubular members 20, 30, 40, other numbers of tubular members may also be employed, like two tubular members, or four or more tubular members. The tubular members may be adhesively bonded in a single procedure (which may include two bonding steps as discussed above), or sequentially. For sequentially bonding the tubular members, an innermost member may first be bonded to a second-most inner member. Then, the second-most inner member may be bonded to the third-most inner member, and so on. Likewise, an outermost member may be bonded to a second-most outer member first, and then the second-most outer member is bonded to the third-most outer member, and so on.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. An endoscope comprising:

a handle, an elongated shaft, and a video camera disposed in the shaft, wherein the elongated shaft comprising a plurality of nested tubes, the plurality of nested tubes comprising a first tube, a second tube at least partially disposed within the first tube, and a third tube disposed between the first tube and the second tube, the first tube, the second tube and the third tube being fixed to one another through adhesive bonding, the first tube having a first bore formed in the first tube, the third tube having a second bore formed in the third tube, the second bore overlapping the first bore;

the first bore and the second bore being in communication with a first gap between the first tube and the third tube and with a second gap between the third tube and the second tube; and an adhesive provided in the first gap and in the second gap.

2. The endoscope of claim 1, wherein the plurality of nested tubes sealingly houses the video camera.

3. The endoscope of claim 1, wherein the adhesive is provided in one or more of the first gap in a first area surrounding the first bore and the second gap in a second area surrounding the second bore.

4. The endoscope of claim 1, wherein the second tube comprises a recess in an area corresponding to the second bore.

5. The endoscope of claim 1, wherein the first bore comprises a plurality of first bores formed along a circumference of the first tube.

6. The endoscope of claim 1, wherein the adhesive further fully extends around one or more of an outer circumference of the second tube and an outer circumference of the third tube.

7. The endoscope of claim 1, wherein the second bore has a second diameter smaller than a first diameter of the first bore.

8. The endoscope of claim 1, wherein the second bore is offset from the first bore such that the second bore partially overlaps with the first bore.

9. The endoscope of claim 1, wherein the second bore has a second diameter larger than a first diameter of the first bore.

10. The endoscope of claim 5, wherein the adhesive comprises a first adhesive applied in a first area of at least a first one of the plurality of first bores, and a second adhesive, different from the first adhesive, applied in a second area of at least a second one of the plurality of first bores.

11. The endoscope of claim 10, wherein the first adhesive is a UV-setting adhesive.

12. The endoscope of claim 11, wherein the second adhesive is a thermosetting adhesive agent.

13. The endoscope of claim 10, wherein a second glass transition temperature of the second adhesive is higher than a first glass transition temperature of the first adhesive.

14. The endoscope of claim 1, wherein one or more of the first bore is disposed in a first wall of the first tube and the second bore is disposed in a second wall of the third tube.

15. The endoscope of claim 1, wherein one or more of the first gap has a first annular shape and the second gap has a second annular shape.

16. The endoscope of claim 1, wherein an overlap between the first bore and the second bore is in one or more of a circumferential direction and a longitudinal direction.

17. The endoscope of claim 1, wherein the recess comprises a flat portion on an outer circumferential surface of the second tube.

18. The endoscope of claim 1, wherein the second tube further comprises a third bore offset longitudinally from the second bore, the third bore being in communication with the second gap between the second tube and the third tube; and the adhesive comprising a first adhesive, the endoscope further comprising a second adhesive provided in the third gap.

19. The endoscope of claim 18, wherein the second tube comprises a recess in an area corresponding to the third bore.

20. The endoscope of claim 19, wherein the recess comprises a flat portion on an outer circumferential surface of the second tube.

* * * * *